(12) United States Patent
Meffert et al.

(10) Patent No.: US 6,331,294 B1
(45) Date of Patent: Dec. 18, 2001

(54) USE OF COPOLYMERS OF MONOETHYLENICALLY UNSATURATED CARBOXYLIC ACIDS AS SOLUBILIZERS

(75) Inventors: Helmut Meffert, Mannheim; Axel Sanner, Frankenthal; Gunther Berndl, Herxheim; Folker Ruchatz, Neustadt; Karl Kolter, Limburgerhof; Kurt Heinz Bauer, Freiburg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/268,720

(22) Filed: Mar. 17, 1999

(30) Foreign Application Priority Data

Mar. 18, 1998 (DE) ................................ 198 11 919

(51) Int. Cl.⁷ ........................ A61K 31/74; C08F 220/52; C08F 220/04
(52) U.S. Cl. .................. 424/78.03; 424/401; 424/78.02
(58) Field of Search ................ 424/78.03, 401, 424/78.02

(56) References Cited

U.S. PATENT DOCUMENTS

| | | | |
|---|---|---|---|
| 3,915,921 | 10/1975 | Schlatzer, Jr. | 260/17 |
| 3,936,427 * | 2/1976 | Viout et al. | |
| 4,395,524 | 7/1983 | Emmons et al. | 526/307 |
| 4,432,881 | 2/1984 | Evani | 252/8.5 |
| 4,911,736 | 3/1990 | Huang et al. | 44/51 |
| 5,004,598 | 4/1991 | Lochhead et al. | 424/59 |
| 5,324,765 | 6/1994 | Mondet et al. | 524/423 |

FOREIGN PATENT DOCUMENTS

| | | |
|---|---|---|
| 268 164 A2 | 5/1988 | (EP) . |
| 268164 | 5/1988 | (EP) . |
| 0268164 B1 * | 5/1988 | (EP) . |
| 494 022 A1 | 7/1992 | (EP) . |
| WO 93/22357 | 11/1993 | (WO) . |

OTHER PUBLICATIONS

Book of Chem Abstracts, 210$^{th}$ ACS Meeting Aug. 20–24, (1995) Lochead et al. Sheer Enhanced Emulsification of Oil by Hydrophobically–modified poly(acrylic) acid.*
Lorenz et al., *Agents and Actions*, vol. 12, ½ (1982), pp. 64–79.
G. Eisenmann, Dissertation (Prof. Bauer, Freiburg Univ, 1994, pp. 44–45 and 93–95.
Tribet et al., *Proc. Natl. Acad. Sci. USA*, vol. 93, pp. 15047–15050, Dec. 1996.

\* cited by examiner

Primary Examiner—Thurman K. Page
Assistant Examiner—Brian K. Seidleck
(74) Attorney, Agent, or Firm—Keil & Weinkauf

(57) ABSTRACT

The invention relates to the use of copolymers comprising a) 82 to 99.9 mol % of at least one monoethylenically unsaturated $C_3$–$C_8$-carboxylic acid;
b) 0.1 to 18 mol % of at least one monomer selected from the group
  $b_1$) N—$C_8$–$C_{30}$-alkyl-substituted amides of monoethylenically unsaturated $C_3$–$C_8$-carboxylic acids,
  $b_2$) N,N—$C_8$–$C_{30}$-dialkyl-substituted amides of monoethylenically unsaturated $C_3$–$C_8$-carboxylic acids,
  $b_3$) $C_8$–$C_{30}$-alkyl esters of monoethylenically unsaturated $C_3$–$C_8$-carboxylic acids;
c) 0 to 17.9 mol % of at least one monomer selected from the group of
  $c_1$) vinyl esters of aliphatic $C_8$–$C_{30}$-carboxylic acids,
  $c_2$) $C_8$–$C_{30}$-alkylvinyl ethers,
mol % data for the individual components adding up to 100%, as solubilizer.

9 Claims, No Drawings

USE OF COPOLYMERS OF MONOETHYLENICALLY UNSATURATED CARBOXYLIC ACIDS AS SOLUBILIZERS

The invention relates to the use of copolymers of monoethylenically unsaturated carboxylic acids as solubilizers.

In the manufacture of homogeneous pharmaceutical or cosmetic preparations, the solubilization of hydrophobic substances has achieved very great practical importance.

Solubilization is taken to mean an improvement in the solubility by virtue of surface-active compounds which can convert substances which are insoluble or virtually insoluble in water into clear, at most opalescent aqueous solutions without changing the chemical structure of these substances in the process.

The solubilizates formed are notable for the fact that the substance which is insoluble or virtually insoluble in water is present in dissolved form in the molecular associations of the surface-active compounds which form in aqueous solution, also called micelles. The resulting solutions are stable single-phase systems which appear optically clear to opalescent and can be prepared without the input of energy.

Solubilizers can, for example, improve the appearance of cosmetic formulations and food preparations by making the formulations transparent. Furthermore, in the case of pharmaceutical preparations, the bioavailability and thus the activity of medicaments can also be increased by using solubilizers.

The principal solubilizers used for pharmaceutical medicaments and cosmetic active ingredients are the following products:

ethoxylated (hydrogenated) castor oil, (e.g. Cremophor® products, BASF);

ethoxylated sorbitan fatty acid esters, (e.g. Tween® products, ICI);

ethoxylated hydroxystearic acid, (e.g. Solutol® products, BASF).

The above-described hitherto used solubilizers do, however, exhibit a number of technical disadvantages.

For example, their parenteral application, is associated with the release of histamine and a consequent drop in blood pressure (Lorenz et al., Agents and Actions, Vol. 12, 1/2, 1982).

The known solubilizers only have a low solubilizing action for some virtually insoluble medicaments, such as, for example, clotrimazole.

Surface-active compounds frequently have high haemolytic activity, which prevents use in the pharmaceutical field, in particular in substances administered parenterally.

The dissertation by G. Eisenmann (Prof. Bauer, Freiburg University, 1994, page 44/45, 93 to 95) describes the polymer-analogous reaction of polyacrylic acid having a $M_w \approx 2000$ with. linear alkylamines of chain length $C_6$ to $C_8$ with activation of the carboxyl groups using dicyclohexylcarbodiimide to give the corresponding amides. The proportion of amidated carboxyl groups is between 20% and 33%. However, the copolymers described here as solubilizers have the disadvantage that they are insufficiently soluble in water at concentrations >5% by weight.

C. Tribet et al. (Proc. Natl. Acad. Sci. 1996, 93, 15047–15050) describe polyacrylic acid reacted with octylamine and isopropylamine in a polymer-analogous manner which has a molecular weight of $M_w \approx 8000$ to 34,000. Its profile of properties (insufficient solubility in water, too low a solubilizing action) indicates that these polymers are unsatisfactory for use as solubilizers in pharmaceutical and cosmetic preparations.

U.S. Pat. No. 4,432,881 describes hydrophobically modified polyacrylic acid having a molecular weight between 200,000 and 5,000,000, which are obtained by copolymerization of acrylic acid with the corresponding N-alkylacrylamides or acrylates. The resulting polymers are used as dispersible hydrophobic thickeners.

U.S. Pat. No. 4,395,524 describes the copolymerization of hydrophilic components (e.g. acrylamide, acrylic acid, N-vinylpyrrolidone etc.) with N-alkylacrylamides. The resulting polymers having a molecular weight of from 30,000 to 2,000,000 are used as thickeners, sedimentation stabilizers or dispersants.

EP-A-0 268 164 describes the use of copolymers of mono-olefinically unsaturated acids and alkyl esters of mono-olefinically unsaturated acids for the stabilization of O/W emulsions.

It is an object of the present invention to provide novel solublizers for pharmaceutical, cosmetic and food applications which do not have the abovementioned disadvantages.

We have found that this object is achieved by the use of copolymers comprising a) 82 to 99.9 mol % of at least one monoethylenically unsaturated $C_3$–$C_8$-carboxylic acid;

b) 0.1 to 18 mol % of at least one monomer selected from the group $b_1$) N—$C_8$–$C_{30}$-alkyl-substituted amides of monoethylenically unsaturated $C_3$–$C_8$-carboxylic acids, $b_2$) N,N—$C_8$–$C_{30}$-dialkyl-substituted amides of monoethylenically unsaturated $C_3$–$C_8$-carboxylic acids,.

$b_3$) $C_8$–$C_{30}$-alkyl esters of monoethylenically unsaturated $C_3$–$C_8$-carboxylic acids;

c) 0 to 17.9 mol % of at least one monomer selected from the group of $c_1$) vinyl esters of aliphatic $C_8$–$C_{30}$-carboxylic acids, $c_2$) $C_8$–$C_{30}$-alkylvinyl ethers, the mol % data for the individual components adding up to 100%, as solubilizer.

As hydrophilic component a), the following copolymerizable monomers may be mentioned:

monoethylenically unsaturated carboxylic acids having from 3 to 8 carbon atoms, such as, for example, acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid.

From this group of monomers, preference is given to using acrylic acid, methacrylic acid, maleic acid or mixtures of said carboxylic acids.

The monoethylenically unsaturated carboxylic acids can be used in the copolymerization as free acid, as anhydrides and also in partially or completely neutralized form.

For the neutralization of the abovementioned carboxylic acids, alkali metal or alkaline earth metal bases, ammonia or amines are advantageously used, preferably sodium hydroxide solution, potassium hydroxide solution, soda, potash, sodium hydrogencarbonate, magnesium oxide, calcium hydroxide, calcium oxide, gaseous or aqueous ammonia, triethylamine, ethanolamine, diethanolamine, triethanolamine, morpholine, diethylenetriamine or tetraethylenepentamine.

Other comonomers which can be used are the following copolymerizable, hydrophilic monomers in amounts of from 0 to 17.9 mol %, preferably from 0 to 14.9 mol %, particularly preferably from 0 to 12.9 mol %:

acrylamidoglycolic acid, vinylsulfonic acid, allylsulfonic acid, methallylsulfonic acid, styrenesulfonic acid, 3-sulfopropyl acrylate, 3-sulfopropyl methacrylate and acrylamido methylpropanesulfonic acid;

monomers containing phosphonic acid groups, such as vinylphosphonic acid, allylphosphonic acid and acrylamidomethanepropanephosphonic acid;

N-vinylpyrrolidone, N-vinylcaprolactam, N-vinylimidazole, N-vinyl-2-methylimidazole and N-vinyl-4-methylimidazole.

It is of course also possible to use mixtures of said monomers.

The proportion of hydrophilic monomer units a) in the copolymer is in the range from 82 to 99.9 mol %, preferably from 85 to 95 mol %, particularly preferably in the range from 87 to 93 mol %.

As hydrophobic components b), the following polymerizable comonomers may be mentioned:

N—$C_8$–$C_{30}$-alkyl- or N,N—$C_8$–$C_{30}$-dialkyl-substituted amides of monoethylenically unsaturated $C_3$–$C_8$-carboxylic acids, the alkyl radicals being aliphatic or cycloaliphatic alkyl radicals having from 8 to 30, preferably from 8 to 18, carbon atoms.

The monoethylenically unsaturated carboxylic acids having from 3 to 8 carbon atoms are understood to include the acids already mentioned above, preferably acrylic acid, methacrylic acid, dimethacrylic acid, ethacrylic acid, maleic acid, citraconic acid, methylenemalonic acid, allylacetic acid, vinylacetic acid, crotonic acid, fumaric acid, mesaconic acid and itaconic acid.

From this group of monomers, acrylic acid, methacrylic acid, maleic acid or mixtures of said carboxylic acids are likewise used particularly preferably.

Preferred amidated comonomers are, for example, N-stearylacrylamide, N-stearylmethacrylamide, N-(1-methyl) undecylacrylamide, N-(1-methyl) undecylmethacrylamide, N-dodecylacrylamide, N-dodecylmethacrylamide, N-octylacrylamide, N-octylmethacrylamide, N,N-dioctylacrylamide, N,N-dioctylmethacrylamide, N-cetylacrylamide, N-cetylmethacrylamide, N-dodecylacrylamide, N-dodecylmethacrylamide, N-myristylacrylamide, N-myristylmethacrylamide, N-(2-ethyl)hexylacrylamide and N-(2-ethyl)hexylmethacrylamide.

If maleic anhydride is the comonomer, it can be reacted in a polymer-analogous manner with N-alkylamines by ring opening to give the corresponding amides.

Other hydrophobic comonomers b) used can be monoethylenically unsaturated $C_3$–$C_8$-carboxylic esters with a $C_8$–$C_{30}$-alcohol, preferably a $C_8$–$C_{18}$-alcohol.

Particular importance is attached in this connection to the acrylates and methacrylates with fatty alcohols having a chain length of from 8 to 18 carbon atoms.

The following may be specifically mentioned in this connection: octyl acrylate, 2-ethylhexyl acrylate, nonyl acrylate, decyl acrylate, lauryl acrylate, myristyl acrylate, cetyl acrylate, stearyl acrylate, oleyl acrylate, behenyl acrylate, octyl methacrylate, 2-ethylhexyl methacrylate, nonyl methacrylate, decyl methacrylate, lauryl methacrylate, myristyl methacrylate, cetyl methacrylate, stearyl methacrylate, oleyl methacrylate, behenyl methacrylate and tert-butylcyclohexyl acrylate.

Of the hydrophobic units from group b), particularly preferred representatives are the N—$C_8$–$C_{30}$-alkyl- or N,N—$C_8$–$C_{30}$-dialkyl-substituted amides of monoethylenically unsaturated $C_3$–$C_8$-carboxylic acids.

The amount of hydrophobic monomer units b) in the copolymer is in the range from 0.1 to 18 mol %, preferably from 0.1 to 15 mol %, particularly preferably in the range from 0.1 to 13 mol %.

Further additional components c) which may be used are, where appropriate, vinyl esters of long-chain aliphatic, saturated or unsaturated $C_8$–$C_{30}$-carboxylic acids, such as, for example, caprylic acid, capric acid, lauric acid, myristic acid, palmitic acid, stearic acid, arachidic acid, behenic acid, lignoceric acid, cerotic acid and melissic acid. Preference is given to using vinyl esters of the abovementioned $C_8$–$C_{18}$-carboxylic acids.

In addition, $C_8$–$C_{30}$-alkylvinyl ethers, preferably $C_8$–$C_{18}$-alkylvinyl ethers, can be copolymerized.

Preferred alkyl radicals of the vinyl ethers which may be mentioned are branched or unbranched $C_8$–$C_{18}$-alkyl chains, such as, for example, n-octyl, 2-ethylhexyl, n-nonyl, n-decyl, n-undecyl, n-dodecyl, n-tridecyl, n-tetradecyl, n-pentadecyl, n-hexadecyl, n-heptadecyl and n-octadecyl.

The amount of hydrophobic monomer units c) in the copolymer is in the range from 0 to 17.9 mol %, preferably from 0 to 14.9 mol %, particularly preferably in the range from 0 to 12.9 mol %.

It is of course also possible to polymerize mixtures of the respective monomers from groups a) to c).

In some circumstances it may be appropriate, in addition to the monomer units a) to c) already mentioned, to use further suitable comonomers, for example monoethylenically unsaturated $C_3$–$C_8$-carboxylates of short-chain $C_1$–$C_4$-alcohols, amides and nitriles in amounts of from 0 to 5 mol % for the polymerization.

The following may be mentioned by way of example: methyl acrylate, ethyl acrylate, methyl methacrylate, ethyl methacrylate, hydroxyethyl acrylate, hydroxypropyl acrylate, hydroxybutyl acrylate, hydroxyethyl methacrylate, hydroxypropyl methacrylate, hydroxyisobutyl acrylate, hydroxyisobutyl methacrylate, monomethyl maleate, dimethyl maleate, monoethyl maleate, diethyl maleate, 2-ethylhexyl acrylate, 2-ethylhexyl methacrylate, acrylamide, methacrylamide, N-dimethylacrylamide, N-tert-butylacrylamide, acrylonitrile, methacrylonitrile, dimethylaminoethyl acrylate, diethylaminoethyl acrylate, diethylaminoethyl methacrylate and also the salts of the last-named monomers with carboxylic acids or mineral acids and also the quaternized products.

The copolymers according to the invention have a molecular weight of from 1000 to 30,000 g/mol, preferably from 2000 to 20,000 g/mol, particularly preferably from 3000 to 8000 g/mol.

Applications:

The present invention makes available amphiphilic compounds for use as solubilizers for pharmaceutical and cosmetic preparations and also for food preparations. They have the ability to solubilize virtually insoluble active ingredients in the field of pharmaceuticals and cosmetics, virtually insoluble food supplements, for example vitamins and carotinoids, but also virtually insoluble active ingredients for use in crop-protection compositions and also active ingredients for use in veterinary medicine.

Surprisingly, the claimed compounds have been found to have a good solubilization power for pharmaceutical and cosmetic active ingredients. In addition, the claimed compounds permit applications which are notable for a very low haemolysis rate, and a compatibility free from side effects following parenteral, oral. and topical application to skin and mucosa. In particular, the compounds do not have side effects caused by interactions with blood corpuscle membranes. Following parenteral application there is no, or only a slight, release of histamine. Because of their low molecular weight, the solubilizers are able to pass through the kidneys.

Solubilizers for Cosmetics:

The copolymers according to the invention can be used as solubilizers in cosmetic formulations. For example, they are suitable as solubilizers for cosmetic oils. They have good solubilizing power for fats and oils, such as ground nut oil, jojoba oil, coconut oil, almond oil, olive oil, palm oil, castor oil, soybean oil or wheatgerm oil, or for essential oils, such as dwarf pine oil, lavender oil, rosemary oil, spruce needle oil, pine needle oil, eucalyptus oil, peppermint oil, sage oil, bergamot oil, terpentine oil, melissa oil, juniper oil, citrus oil, aniseed oil, cardamon oil, camphor oil, etc. or for mixtures of these oils.

In addition, the polymers according to the invention can be used as solubilizers for UV absorbers which are insoluble or virtually insoluble in water, such as, for example, 2-hydroxy-4-methoxybenzophenone (Uvinul® M 40, BASF), 2,2',4,4'-tetrahydroxybenzophenone (Uvinul® D 50), 2,2'-dihydroxy-4,4'-dimethoxybenzophenone (Uvinul® D49), 2,4-dihydroxybenzophenone (Uvinul® 400), 2'-ethylhexyl 2-cyano-3,3-diphenylacrylate (Uvinul® N 539), 2,4,6-trianilino-p-(carbo-2'-ethylhexyl-1'-oxy)-1,3,5-triazine (Uvinul® T 150), 3-(4-methoxybenzylidene) camphor (Eusolex® 6300, Merck), 2-ethylhexyl N,N-dimethyl-4-aminobenzoate (Eusolex® 6007), 3,3,5-trimethylcyclohexyl salicylate, 4-isopropyldibenzoylmethane (Eusolex® 8020), 2-ethylhexyl p-methoxycinnamate and 2-isoamyl p-methoxycinnamate and mixtures thereof.

The present invention thus also provides cosmetic preparations which comprise at least one of the copolymers according to the invention having the composition specified at the outset as solubilizers. Preference is given to those preparations which, in addition to the solubilizer, comprise one or more virtually insoluble cosmetic active ingredients, for example the abovementioned oils or UV absorbers.

These formulations are solubilizates based on water or water/alcohol. The solubilizers according to the invention are used in a ratio of from 0.2:1 to 20:1, preferably from 1:1 to 15:1, particularly preferably from 2:1 to 12:1 relative to the virtually insoluble cosmetic active ingredient.

The content of solubilizer according to the invention in the cosmetic preparation is, depending on the active ingredient, in the range from 1 to 50% by weight, preferably from 3 to 40% by weight, particularly preferably from 5 to 30% by weight.

In addition, it is possible to add other auxiliaries to this formulation, for example nonionic, cationic or anionic surfactants, such as alkyl polyglycosides, fatty alcohol sulfates, fatty alcohol ether sulfates, alkanesulfonates, fatty alcohol ethoxylates, fatty alcohol phosphates, alkyl betains, sorbitan esters, POE-sorbitan esters, sugar fatty acid esters, fatty acid polyglyceryl esters, fatty acid partial glycerides, fatty acid carboxylates, fatty alcohol sulfosuccinates, fatty acid sarcosinates, fatty acid isothionates, fatty acid taurinates, citric acid esters, silicone copolymers, fatty acid-polyglycol esters, fatty acid amides, fatty acid alkanolamides, quaternary ammonium compounds, alkylphenol ethoxylates, fatty amine ethoxylates, cosolvents, such as ethylene glycol, propylene glycol, glycerol etc.

Other constituents which may be added are natural or synthetic compounds, for example lanolin derivatives, cholesterol derivatives, isopropyl myristate, isopropyl palmitate, electrolytes, dyes, preservatives, acids (e.g. lactic acid, citric acid).

These formulations can be used, for example, in bath preparations such as bath oils, shaving lotions, face lotions, mouth washes, hair lotions, eau de cologne, eau de toilette and in sunscreen compositions.

Description of the Solubilization Method:

In the preparation of the solubilizates for cosmetic formulations, the copolymers according to the invention can be used as 100% strength substance or, preferably, as aqueous solution.

The solubilizer is usually dissolved in water and thoroughly mixed with the virtually insoluble cosmetic active ingredient to be used in each case.

It is, however, also possible to thoroughly mix the solubilizer with the virtually insoluble cosmetic active ingredient to be used in each case and then to add demineralized water with continuous stirring.

Solubilizers for Pharmaceutical Applications:

The claimed copolymers are likewise suitable for use as solubilizer in pharmaceutical preparations of any type which are distinguished by the fact that they comprise one or more medicaments which are insoluble or virtually insoluble in water, and also vitamins and/or carotinoids. In particular, these are aqueous solutions or solubilizates for oral or, particularly preferably, parenteral application, such as, for example, injection solutions for intravenous, intramuscular or subcutaneous or intraperitoneal application.

Furthermore, the claimed copolymers are suitable for use in oral presentations such as tablets, capsules, powders and solutions. In this case they are able to make available the virtually insoluble medicament with increased bioavailability.

For parenteral application, as well as solubilizates, it is also possible to use emulsions, for example fatty emulsions. For this purpose too, the claimed copolymers are suitable for processing a virtually insoluble medicament.

Pharmaceutical formulations of the above type can be obtained by processing the claimed polymers with pharmaceutical active ingredients by traditional methods and using known and novel active ingredients.

The use according to the invention can additionally include pharmaceutical auxiliaries and/or diluents. Specific auxiliaries are cosolvents, stabilizers and preservatives.

The pharmaceutical active ingredients used are substances which have low or zero solubility in water. According to DAB 9 (German Pharmacopeia), the grading of the solubility of pharmaceutical active ingredients is as follows: slightly soluble (soluble in from 30 to 100 parts of solvent); sparingly soluble (soluble in 20 from 100 to 1000 parts of solvent); virtually insoluble (soluble in more than 10,000 parts of solvent). The active ingredients can be from any of the indicated ranges.

Examples thereof which may be mentioned are benzodiazepines, antihypertensives, vitamins, cytostatics, in particular taxol, anesthetics, neuroleptics, antidepressants, antibiotics, antimycotics, fungicides, chemotherapeutics, urologics, thrombocyte aggregation inhibitors, sulfonamides, spasmolytics, hormones, immunoglobulins, sera, thyroid therapeutic agents, psychopharmacological agents, agents for treating Parkinson's disease and other antihyperkinetic agents, ophthalmics, neuropathy preparations, calcium metabolic regulators, muscle relaxants, antilipemics, hepatic therapeutic agents, coronary agents, cardiacs, immunotherapeutics, regulatory peptides and their inhibitors, hypnotics, sedatives, gynecological agents, gout remedies, fibronolytic agents, enzyme preparations and transport proteins, enzyme inhibitors, emetics, circulation-promoting agents, diuretics, diagnostics, corticoids, cholinergenics, bile duct therapeutics, antiasthmatics, broncholytics, betareceptor blockers, calcium antagonists, ACE inhibitors, arteriosclerotics, antiphlogistics, anticoagulants, antihypotonics, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists and slimming agents.

One possible preparation variant involves the dissolution of the solubilizer in the aqueous phase, optionally with slight warming, and subsequent dissolution of the active ingredient in the aqueous solubilizer solution. The simultaneous dissolution of solubilizer and active ingredient in the aqueous phase is likewise possible.

The copolymers according to the invention can also be used as solubilizers in a manner which, for example, involves dispersing the active ingredient in the solubilizer, optionally with warming, and mixing it with water with stirring.

The invention thus also provides pharmaceutical preparations which comprise at least one of the copolymers according to the invention as solubilizer. Preference is given to preparations which, in addition to the solubilizer, comprise a pharmaceutical active ingredient which is insoluble or virtually insoluble in water, for example from the abovementioned indication fields.

Of the abovementioned pharmaceutical preparations, particular preference is given to those which are formulations which are administered parenterally.

The content of solubilizer according to the invention in the pharmaceutical preparation is, depending on the active ingredient, in the range from 1 to 50% by weight, preferably from 3 to 40% by weight, particularly preferably from 5 to 30% by weight.

Solubilizers for Food Preparations:

As well as use in cosmetics and pharmaceuticals, the copolymers according to the invention are also suitable as solubilizers in the food sector for nutrients, auxiliaries or additives which are insoluble or virtually insoluble in water, such as, for example, fat-soluble vitamins or carotinoids. Examples which may be mentioned are clear drinks colored with carotinoids.

Solubilizers for Crop-protection Preparations:

The use of the copolymers according to the invention as solubilizers in agrochemistry can, inter alia, include formulations which comprise pesticides, herbicides, fungicides or insecticides, especially also preparations of crop-protection agents which can be used as spray or pouring mixtures.

The invention further provides copolymers comprising
a) 82 to 99.9 mol % of at least one monoethylenically unsaturated $C_3$–$C_8$-carboxylic acid;
b) 0.1 to 18 mol % of at least one monomer selected from the group
 $b_1$) N—$C_8$–$C_{30}$-alkyl-substituted amides of monoethylenically unsaturated $C_3$–$C_8$-carboxylic acids,
 $b_2$) N,N—$C_8$–$C_{30}$-dialkyl-substituted amides of monoethylenically unsaturated $C_3$–$C_8$-carboxylic acids,
 $b_3$) C8–$C_{30}$-alkyl esters of monoethylenically unsaturated $C_3$–$C_8$-carboxylic acids;
c) 0 to 17.9 mol % of at least one monomer selected from the group of
 $c_1$) vinyl esters of aliphatic $C_8$–$C_{30}$-carboxylic acids,
 $c_2$) $C_8$–$C_{30}$-alkylvinyl ethers,
the mol % data for the individual components adding up to 100%.

Preference is given to copolymers comprising
a) 85 to 95 mol % of at least one monoethylenically unsaturated $C_3$–$C_8$-carboxylic acid;
b) 0.1 to 15 mol % of at least one monomer selected from the group
 $b_1$) N—$C_{12}$–$C_{22}$-alkyl-substituted amides of monoethylenically unsaturated $C_3$–$C_8$-carboxylic acids,
 $b_2$) N,N—$C_{12}$–$C_{22}$-dialkyl-substituted amides of monoethylenically unsaturated $C_3$–$C_8$-carboxylic acids,
 $b_3$) $C_8$–$C_{18}$-alkyl esters of monoethylenically unsaturated $C_3$–$C_8$-carboxylic acids;
c) 0 to 14.9 mol % of at least one monomer selected from the group of
 $c_1$) vinyl esters of aliphatic $C_8$–$C_{18}$-carboxylic acids,
 $c_2$) $C_8$–$C_{18}$-alkylvinyl ethers,
the mol % data for the individual components adding up to 100%.

For the general and preferred definition of the individual monomer units a) to c) and for the composition and the molecular weight of the copolymers according to the invention, reference is made to the description already given at the outset.

The copolymers have K values of at least 7, preferably from 10 to 30, particularly preferably 10–25. The K values are determined in accordance with H. Fikentscher, Cellulose-Chemie, Volume 13 (1932), 58 to 64 and 71 to 74 in aqueous solution at 25° C., at concentrations which, depending on the K value range, are between 0.1% and 5%.

The copolymers are prepared by radically polymerizing the corresponding monomers.

The preparation is carried out by known processes, e.g. solution, precipitation, or inverse suspension polymerization using compounds which form free radicals under the polymerization conditions.

The polymerization temperatures are usually in the range from 30 to 200° C., preferably from 40 to 110° C. Examples of suitable initiators are azo and peroxy compounds and also the customary redox initiator systems, such as combinations of hydrogen peroxide and reducing compounds, e.g. sodium sulfite, sodium bisulfite, sodium formaldehyde sulfoxylate and hydrazine.

The reaction medium used is any customary solvent in which the monomers are soluble. Preference is given to alcoholic solvents, such as, for example, methanol, ethanol, n-propanol or isopropanol.

In order to ensure that the reaction gives homogeneous products, it is advantageous to introduce the monomers and the initiator into the reaction solution separately. This can be achieved, for example, using separate feed lines for the individual reactants.

The solids content in the resulting organic solution is usually from 20 to 60% by weight, in particular from 25 to 40% by weight.

The solvent used for the polymerization can then be removed using steam distillation and be exchanged for water.

The aqueous solutions of the copolymers can, by various drying processes such as, for example, spray-drying, fluidized spray-drying, roller drying or freeze drying, be converted into powder form, which can be used to prepare an aqueous dispersion or solution by redispersion in water.

The following examples illustrate the preparation and use of the copolymers according to the invention in more detail.

EXAMPLE 1

Preparation of an Acrylic Acid-stearyl Methacrylate Copolymer (89.7 : 10.3 mol %)

10 g of acrylic acid in 350 g of isopropanol were introduced into a 2 liter glass flask which had been flushed with nitrogen and had four separate feed devices. Feed 1 comprised 140 g of stearyl methacrylate in 400 g of isopropanol, feed 2 comprised 250 g of acrylic acid in 400 g of isopropanol, feed 3 comprised 19 g of tert-butyl perpivalate (75% strength solution) in 100 g of isopropanol and feed 4 comprised 5.3 g of tert-butyl perpivalate (75% strength) in isopropanol. The initial charge was stirred under protective gas at 80° C. Feed 1 was introduced over 5.5 hours, feed 2 over 6 hours and feed 3 over 6.5 hours. After a further hour, feed 4 was added over one hour. The mixture was then left to afterpolymerize for one hour. The isopropanol was then exchanged for water by steam distillation. The aqueous suspension was adjusted to pH 7 using sodium hydroxide solution. This gave a clear solution of the polymer having a solids content of 20.7%.

EXAMPLE 2

Preparation of an Acrylic Acid-N-octadecylacrylamide Copolymer (92 : 8 mol %)

10 g of acrylic acid in 250 g of isopropanol were introduced into a 2 liter glass flask which had been flushed with nitrogen and had four separate feed devices. Feed 1 comprised 55 g of N-octadecylacrylamide in 300 g of isopropanol, feed 2 comprised 131 g of acrylic acid in 100 g of isopropanol, feed 3 comprised 9 g of tert-butyl perpivalate (75% strength solution) in 50 g of isopropanol and feed 4 comprised 2.5 g of tert-butyl perpivalate (75% strength) in isopropanol. The initial charge was further flushed with nitrogen and heated to 80° C. with stirring. Feed 1 was introduced over 5.5 hours, feed 2 over 6 hours and feed 3 over 6.5 hours. After a further hour, feed 4 was added over one hour. The mixture was then left to afterpolymerize for one hour. The isopropanol was then exchanged for water by steam distillation. The aqueous suspension was adjusted to pH 7 using sodium hydroxide solution. This gave a clear solution of the polymer having a solids content of 16.9%.

Cosmetic Formulations

EXAMPLE 3

6 g of solubilizer, prepared as in Examples 1 and 2, were thoroughly mixed with 1 g of each of the essential oils or perfume oils listed in Table 1 using a magnetic stirrer. With continuous stirring, a burette was used to slowly add demineralized water ad 100 g. The resulting formulations had the following composition:

1% by weight of essential or cosmetic oil,
6% by weight of solubilizer,
93% by weight of water

TABLE 1

| Solubilizer | Essential oil | Appearance of the formulation |
| --- | --- | --- |
| Example 1 | Spruce needle oil | Opalescent solubilizate |
| Example 1 | Rosemary oil | Opalescent solubilizate |
| Example 1 | Lavender oil | Clear solubilizate |
| Example 1 | "Minos" aftershave from Drom | Opalescent solubilizate |
| Example 2 | Dwarf pine oil | Clear solubilizate |
| Example 2 | Lavender oil | Opalescent solubilizate |

EXAMPLE 4

Sunscreen Compositions 25 g of copolymer, prepared as in Example 2, were dissolved at about 60° C. in a mixture of 62.5 g of bidistilled water and 10 g of glycerol, and 2.5 g of the sunscreen Uvinul® T 150 (BASF) was added to the solution at 60° C. with gentle stirring. A clear solution formed which, after cooling to room temperature, was drawn off.

EXAMPLE 5

Solubilizing Action Using Diazepam as an Example

Excess diazepam was in each case added to 1% by weight strength polymer solutions of the copolymers given in Table 2 (in phosphate buffer pH 7). With continuous shaking, an equilibrium between polymer, active ingredient and water was established. The excess solid was filtered off. The content of active ingredient in the filtrate was determined.

TABLE 2

| Copolymer | Solubilization |
| --- | --- |
| Acrylic acid-N-stearylacrylamide (90:10% by weight), Na salt | 160 µg/ml of diazepam |
| Acrylic acid-N-stearylacrylamide (90:10% by weight), K salt | 269 µg/ml of diazepam |
| Acrylic acid-N-stearylacrylamide (80.9:19.1% by weight), Na salt | 317 µg/ml of diazepam |
| Acrylic acid-N-stearylacrylamide (80.9:19.1% by weight), K salt | 222 µg/ml of diazepam |
| Acrylic acid-N-stearylacrylamide (62.5:37.5% by weight), Na salt | 433 µg/ml of diazepam |
| Acrylic acid-N-stearylacrylamide (66.8:33.2% by weight), Na salt | 436 µg/ml of diazepam |
| Acrylic acid-N-stearylacrylamide (73.5:26.5% by weight), Na salt | 375 µg/ml of diazepam |
| Acrylic acid-N-stearylacrylamide (66.7:33.3% by weight), Na salt Comparison | 361 µg/ml of diazepam |
| Phosphate buffer, pH 7.0 | 50 µg/ml of diazepam |

EXAMPLE 6

Solubilizing Action Using 17-β-estradiol and Clotrimazole as Examples

17-β-Estradiol and clotrimazole were in each case added in excess to a 10% by weight strength polymer solution [acrylic acid-N-stearylacrylamide copolymer, (90:10% by weight) in phosphate buffer pH 7.0], heated to 65° C., and the mixture was slowly stirred until equilibrium was established. The excess solid was filtered off, and the content of dissolved active ingredient in the filtrate was determined (see Table 3).

TABLE 3

| | Solubilization [% by weight] | |
| --- | --- | --- |
| Copolymer | 17-β-Estradiol | Clotrimazole |
| Acrylic acid-N-stearylacrylamide (90:10% by weight), Na salt Comparison: | 0.14 | 0.24 |
| Phosphate buffer, pH 7.0 | 0.0 | 0.0 |
| Tween ® 80 | 0.045 | 0.015 |
| Cremophor ® EL | 0.03 | 0.05 |

EXAMPLE 7

Diazepam Injection Solution 250 mg of acrylic acid-N-stearylacrylamide copolymer (66.8:33.2% by weight), Na salt were dissolved in 1728 mg of bidistilled water. 10 mg of diazepam were then added to the solubilizer solution and stirred until the medicament had dissolved. The solution was preserved using 2 mg of sodium disulfite and 10 mg of benzyl alcohol and sterilized by filtration using customary methods and poured into injection vials.

EXAMPLE 8

17-β-Estradiol Gelatin Capsules 100 mg of 17-β-estradiol were mixed with 10 g of acrylic acid-N-stearylacrylamide copolymer (90:10% by weight), Na salt, 80 g of molten PEG 6000 and 10 g of ethanol, and the mixture was then transferred directly in liquid form to capsules.

EXAMPLE 9

Diazepam Emulsion for Parenteral Application 80 g of acrylic acid-N-stearylacrylamide copolymer (66.8:33.2% by weight) were dissolved in 720 g of bidistilled water. 10 g of diazepam were dispersed in a 1:1 mixture of soybean oil and miglyol oil (oil phase was 200 g). In addition, 10 g of soybean lecithin were used, which were dissolved in the oil phase. The two phases were predispersed and then emulsified by high-pressure homogenization.

EXAMPLE 10

17-β-Estradiol Tablets 10 g of 17-β-estradiol were mixed with 200 g of acrylic acid-N-stearylacrylamide copolymer (90:10% by weight) and 290 g of Ludipress® (BASF) and 0.5 g of magnesium stearate. The mixture was then tableted directly.

We claim:

1. A method of solubilizing pharmaceutical and/or cosmetic preparations based on water or water/alcohol which comprises adding to those preparations 1 to 50% by weight of a copolymer with a molecular weight of from 1000 to 30,000 g/mol comprising
   a) 82 to 99.9 mol % of at least one monoethylenically unsaturated carboxylic acid selected from the group of acrylic acid, methacrylic acid and maleic acid;
   b) 0.1 to 18 mol % of at least one monomer selected from the group
      $b_1$) N,N—$C_8$–$C_{30}$-alkyl-substituted amides of monoethylenically unsaturated carboxylic acids selected from the group of acrylic acid, methacrylic acid and maleic acid,
      $b_2$) N,N—$C_8$–$C_{30}$-dialkyl-substituted amides of monoethylenically unsaturated carboxylic acids selected from the group of acrylic acid, methacrylic acid and maleic acid,
      $b_3$) $C_8$–$C_{30}$-alkyl-esters of acrylic acid or methacrylic acid;
   c) 0 to 17.9 mol % of at least one monomer selected from the group of
      $c_1$) vinyl esters of aliphatic $C_8$–$C_{30}$-carboxylic acids,
      $c_2$) $C_8$–$C_{30}$-alkylvinyl ethers, the mol % data for the individual components adding up to 100%, as solubilizer.

2. A method as claimed in claim 1, wherein the copolymer comprises
   a) 85 to 95 mol % of at least one monoethylenically unsaturated $C_8$–$C_{30}$-carboxylic acid selected from the group of acrylic acid, methacrylic acid and maleic acid;
   b) 0.1 to 15 mol % of at least one monomer selected from the group
      $b_1$) a member slected from the group consisting of N-stearylacrylamide, N-stearylmethacrylamide, N-(1-methyl) undecylacrylamide, N-(1-methyl) undecylmethacrylamide, N-dodecylcrylamide, N-dodecylmethacrylamide, N-octylcrylamide, N-octylmethacrylamide, N-cetylcrylamide, N-cetylmethacrylamide, N-myristylacrylamide, N-myristylmethacrylamide, N-(2-ethyl) hexylacrylamide and N-(2-ethyl) hexyl-methacrylamide,
      $b_2$) N,N-dioctylacrylamide, or N-dioctylmethacrylamide,
      $b_3$) a member selected from the group consisting of octyl acrylate, 2-ethylhexyl acrylate, nonyl acrylate, decyl acrylate, lauryl acrylate, myristyl acrylate, cetyl acrylate, stearyl acrylate, oleyl acrylate, behenyl acrylate, octyl methacrylate, 2-ethylhexyl methacrylate, nonyl methacrylate, decyl methacrylate, lauryl methacrylate, myristyl methacrylate, cetyl methacrylate, stearyl methacrylate, oleyl methacrylate, behenyl methacrylate, and tert-butylcyclohexyl acrylate;
   c) 0 to 14.9 mol % of at least one monomer selected from the group of
      $c_1$) a vinyl ester selected from the group consisting of caprylic acid, capric acid, lauric acid, myristic acid, palmitic acid, stearic acid, arachidic acid, behenic acid, lignoceric acid, cerotic acid and melissic acid,
      $c_2$) n-octyl-, 2-ethylhexyl-, n-nonyl, n-decyl, n-undecyl, n-dodecyl, n-tridecyl-, n-etradecyl-,n-pentadecyl, n-hexadecyl, n-heptadecyl-, and N-octadecylvinyl ethers, the mol % data for the individual components adding up to 100%, as solubilizer.

3. A pharmaceutical preparation comprising at least one of the polymers as defined in claim 1 as solubilizer.

4. A preparation as claimed in claim 3 comprising a pharmaceutical active ingredient which is insoluble or virtually insoluble in water.

5. A preparation as claimed in claim 3 in a parenterally administrable presentation.

6. A cosmetic preparation comprising at least one of the polymers as defined in claim 1.

7. A preparation as claimed in claim 6 comprising a cosmetic active ingredient which is insoluble or virtually insoluble in water.

8. A preparation as claimed in claim 7 in the form of a solubilizate based on water or water/alcohol.

9. A preparation as claimed in claim 6 comprising a cosmetic active ingredient which is insoluble or virtually insoluble in water.

* * * * *